US008280510B2

United States Patent
Dyjach et al.

(10) Patent No.: US 8,280,510 B2
(45) Date of Patent: *Oct. 2, 2012

(54) METHOD FOR EXCLUSION OF ECTOPIC EVENTS FROM HEART RATE VARIABILITY METRICS

(75) Inventors: John A. Dyjach, Circle Pines, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/167,621

(22) Filed: Jun. 23, 2011

(65) Prior Publication Data

US 2011/0257698 A1    Oct. 20, 2011

Related U.S. Application Data

(63) Continuation of application No. 12/235,868, filed on Sep. 23, 2008, now Pat. No. 7,970,467, which is a continuation of application No. 10/728,124, filed on Dec. 4, 2003, now Pat. No. 7,428,436, and a continuation-in-part of application No. 10/436,876, filed on May 12, 2003, now Pat. No. 7,069,070, and a continuation-in-part of application No. 09/802,316, filed on Mar. 8, 2001, now Pat. No. 6,678,547, and a continuation-in-part of application No. 10/035,009, filed on Dec. 28, 2001, now Pat. No. 7,062,314, which is a continuation-in-part of application No. 09/704,844, filed on Nov. 2, 2000, now Pat. No. 6,718,197.

(51) Int. Cl.
*A61N 1/00* (2006.01)

(52) U.S. Cl. .......................................................... 607/9
(58) Field of Classification Search ..................... 607/9
See application file for complete search history.

(56) References Cited

U.S. PATENT DOCUMENTS

| 5,291,400 A | 3/1994 | Gilham |
| 5,560,370 A | 10/1996 | Verrier et al. |
| 5,603,331 A | 2/1997 | Heemels et al. |
| 5,645,570 A | 7/1997 | Corbucci |
| 5,682,901 A | 11/1997 | Kamen |
| 5,749,900 A | 5/1998 | Schroeppel et al. |
| 5,755,671 A | 5/1998 | Albrecht et al. |

(Continued)

FOREIGN PATENT DOCUMENTS

EP    0555988    8/1993

(Continued)

OTHER PUBLICATIONS

"U.S. Appl. No. 10/695,430, Non-Final Office Action mailed Sep. 9, 2008", 5 pgs.

(Continued)

*Primary Examiner* — George Manuel
(74) *Attorney, Agent, or Firm* — Schwegman, Lundberg & Woessner, P.A.

(57) ABSTRACT

Heart rate variability metrics are derived from the intervals between successive heart beats, referred to as BB intervals. A method implementable by an implantable cardiac device for excluding BB intervals due to ectopic beats based on a function of preceding BB intervals is presented. It is desirable to remove such BB intervals from a BB interval time series used to calculate a heart rate variability metric.

20 Claims, 3 Drawing Sheets

U.S. PATENT DOCUMENTS

| | | | |
|---|---|---|---|
| 5,842,997 | A | 12/1998 | Verrier et al. |
| 5,891,044 | A | 4/1999 | Golosarsky et al. |
| 5,921,940 | A | 7/1999 | Verrier et al. |
| 5,941,831 | A | 8/1999 | Turcott |
| 5,978,707 | A | 11/1999 | Krig et al. |
| 6,022,322 | A | 2/2000 | Prutchi |
| 6,026,320 | A | 2/2000 | Carlson et al. |
| 6,035,233 | A | 3/2000 | Schroeppel et al. |
| 6,042,548 | A | 3/2000 | Giuffre |
| 6,044,294 | A | 3/2000 | Mortazavi et al. |
| 6,056,742 | A | 5/2000 | Murphy-Chutorian et al. |
| 6,144,878 | A | 11/2000 | Schroeppel et al. |
| 6,151,524 | A | 11/2000 | Krig et al. |
| 6,216,032 | B1 | 4/2001 | Griffin et al. |
| 6,224,553 | B1 | 5/2001 | Nevo |
| 6,240,314 | B1 | 5/2001 | Plicchi et al. |
| 6,246,909 | B1 | 6/2001 | Ekwall |
| 6,269,263 | B1 | 7/2001 | Ohnishi et al. |
| 6,272,377 | B1 | 8/2001 | Sweeney et al. |
| 6,317,632 | B1 | 11/2001 | Krig et al. |
| 6,358,201 | B1 | 3/2002 | Childre et al. |
| 6,390,986 | B1 | 5/2002 | Curcie et al. |
| 6,430,441 | B1 | 8/2002 | Levine |
| 6,453,201 | B1 | 9/2002 | Daum et al. |
| 6,456,880 | B1 | 9/2002 | Park et al. |
| 6,459,929 | B1 | 10/2002 | Hopper et al. |
| 6,463,326 | B1 | 10/2002 | Hartley et al. |
| 6,470,210 | B1 | 10/2002 | Chen et al. |
| 6,473,644 | B1 | 10/2002 | Terry, Jr. et al. |
| 6,480,733 | B1 | 11/2002 | Turcott |
| 6,487,450 | B1 | 11/2002 | Chen et al. |
| 6,493,585 | B2 | 12/2002 | Plicchi et al. |
| 6,511,500 | B1 | 1/2003 | Rahme |
| 6,512,957 | B1 | 1/2003 | Witte |
| 6,522,914 | B1 | 2/2003 | Huvelle |
| 6,529,772 | B2 | 3/2003 | Carlson et al. |
| 6,564,096 | B2 | 5/2003 | Mest |
| 6,571,121 | B2 | 5/2003 | Schroeppel et al. |
| 6,571,122 | B2 | 5/2003 | Schroeppel et al. |
| 6,594,523 | B1 * | 7/2003 | Levine ............... 607/30 |
| 6,611,713 | B2 | 8/2003 | Schauerte |
| 6,647,289 | B2 | 11/2003 | Prutchi |
| 6,678,547 | B2 | 1/2004 | Carlson et al. |
| 6,690,970 | B1 | 2/2004 | Taheri et al. |
| 6,690,971 | B2 | 2/2004 | Schauerte et al. |
| 6,709,390 | B1 | 3/2004 | Marie Pop |
| 6,711,440 | B2 | 3/2004 | Deal et al. |
| 6,721,599 | B2 | 4/2004 | De Vries |
| 6,748,261 | B1 | 6/2004 | Kroll et al. |
| 6,752,765 | B1 | 6/2004 | Jensen et al. |
| 6,824,538 | B2 | 11/2004 | Chen |
| 6,865,414 | B1 | 3/2005 | Levine |
| 6,941,332 | B2 | 9/2005 | Jensen |
| 7,062,314 | B2 | 6/2006 | Zhu et al. |
| 7,069,070 | B2 | 6/2006 | Carlson et al. |
| 7,079,888 | B2 | 7/2006 | Oung et al. |
| 7,207,947 | B2 | 4/2007 | Koh et al. |
| 7,428,436 | B2 | 9/2008 | Dyjach et al. |
| 7,572,226 | B2 | 8/2009 | Scheiner et al. |
| 7,970,467 | B2 | 6/2011 | Dyjach et al. |
| 2002/0016550 | A1 | 2/2002 | Sweeney et al. |
| 2002/0026222 | A1 | 2/2002 | Schauerte et al. |
| 2002/0029000 | A1 | 3/2002 | Ohsaki et al. |
| 2002/0058877 | A1 | 5/2002 | Baumann et al. |
| 2002/0072683 | A1 | 6/2002 | Schroeppel et al. |
| 2002/0107552 | A1 | 8/2002 | Krig et al. |
| 2002/0107553 | A1 | 8/2002 | Hill et al. |
| 2002/0116034 | A1 | 8/2002 | Miller et al. |
| 2002/0120304 | A1 | 8/2002 | Mest |
| 2002/0123769 | A1 | 9/2002 | Panken et al. |
| 2003/0097155 | A1 | 5/2003 | Stahmann et al. |
| 2003/0191403 | A1 | 10/2003 | Zhou et al. |
| 2004/0019289 | A1 | 1/2004 | Ross |
| 2004/0230241 | A1 | 11/2004 | Carlson et al. |
| 2005/0090719 | A1 | 4/2005 | Scheiner et al. |

FOREIGN PATENT DOCUMENTS

| | | |
|---|---|---|
| WO | WO-9406350 A1 | 3/1994 |
| WO | WO-9815319 A1 | 4/1998 |
| WO | WO-0044274 A2 | 8/2000 |
| WO | WO-0051680 A1 | 9/2000 |

OTHER PUBLICATIONS

"U.S. Appl. No. 10/695,430, Response filed Oct. 26, 2007 to Office Action mailed Jul. 26, 2007", 7 pgs.

"U.S. Appl. No. 10/695,430, Response filed Dec. 9, 2008 to Non Final Office Action mailed Sep. 9, 2008", 6 pgs.

"U.S. Appl. No. 10/695,430, Response filed Jun. 30, 2008 to Final Office Action mailed Jan. 28, 2008", 6 pgs.

"U.S. Appl. No. 10/728,124, Final Office Action May 9, 2007", 9 pgs.

"U.S. Appl. No. 10/728,124, Non-Final Office Action Feb. 28, 2006", 9 pgs.

"U.S. Appl. No. 10/728,124, Non-Final Office Action mailed Aug. 28, 2007", 12 pgs.

"U.S. Appl. No. 10/728,124, Notice of Allowance mailed May 14, 2008", 6 pgs.

"U.S. Appl. No. 10/728,124, Response filed Jun. 28, 2006 to Non-Final Office Action Feb. 28, 2006", 9 pgs.

"U.S. Appl. No. 10/728,124, Response filed Jul. 9, 2007 to Final Office Action May 9, 2007", 9 pgs.

"U.S. Appl. No. 10/728,124, Response filed Dec. 28, 2007 to Non-Final Office Action mailed Aug. 28, 2007", 12 pgs.

"U.S. Appl. No. 12/235,868 Notice of Allowance mailed Oct. 29, 2010", 7 pgs.

"U.S. Appl. No. 12/235,868, Notice of Allowance mailed Feb. 24, 2011", 5 pgs.

"Heart rate variability: standards of measurement, physiological interpretation and clinical use. Task Force of the European Society of Cardiology and the North American Society of Pacing and Electrophysiology", Circulation, 93(5), (Mar. 1, 1996), 1043-1065.

Behrens, S., "Modification of the Circadian Pattern of Ventricular Tachyarrhythmias by Beta-Blocker Therapy", Clin. Cardiol., 20(3), (Mar. 1997), 253-257.

Berger, R. D., "An Efficient Algorithm for Spectral Analysis of Heart Rate Variability", IEEE Transactions on Biomedical Engineering, BME-33 (9), (Sep. 1986), 900-904.

Bigger, J. T., "Correlations Among Time and Frequency Domain Measures of Heart Period Variability Two Weeks After Acute Myocardial Infarction", Arrhythmias and Conduction Disturbances, 69, (Apr. 1, 1992), 891-898.

Bigger, Jr., J. T., "Spectral Analysis of R-R Variability to Evaluate Autonomic Physiology and Pharmacology and to Predict Cardiovascular Outcomes in Humans", Diagnostic Evaluation, Part XI, Chapter 101, (1992), 1151-1170.

Lavery, C. E., "Nonuniform Nighttime Distribution of Acute Cardiac Events", Circulation, 96(10), (Nov. 18, 1997), 3321-3327.

Vardas, P. E., et al., "Spectral analysis of heart rate variability before and during episodes of nocturnal ischaemia in patients with extensive coronary artery disease", Eur Heart J., 17(3), (Mar. 1996), 388-93.

Yamashita, T., "Circadian Variation of Paroxysmal Atrial Fibrillation", Circulation, 96(5), (Sep. 2, 1997), 1537-1541.

Zhang, Y, et al., "Optimal ventricular rate slowing during atrial fibrillation by feedback AV nodal-selective vagal stimulation", American Journal of Physiology—Heart & Circulatory Physiology, 282(3), (Mar. 2002), H1102-10.

Zhou, X, et al., "Prevention of high incidence of neurally mediated ventricular arrhythmias by afferent nerve stimulation in dogs", Circulation, 101(7), (Feb. 22, 2000), 819-24.

\* cited by examiner

METHOD FOR EXCLUSION OF ECTOPIC EVENTS FROM HEART RATE VARIABILITY METRICS

CROSS REFERENCE TO RELATED APPLICATIONS

This application is a continuation of U.S. application Ser. No. 12/235,868, filed Sep. 23, 2008, now issued as U.S. Pat. No. 7,970,467, which is a continuation of U.S. application Ser. No. 10/728,124, filed Dec. 4, 2003, now issued as U.S. Pat. No. 7,428,436, which application is a continuation-in-part of the following assigned patent applications: U.S. patent application Ser. No. 09/704,844, filed Nov. 2, 2000, now issued as U.S. Pat. No. 6,718,197; U.S. patent application Ser. No. 09/802,316, filed Mar. 8, 2001, now issued as U.S. Pat. No. 6,678,547; U.S. patent application Ser. No. 10/035,009, filed Dec. 28, 2001, now issued as U.S. Pat. No. 7,062,314, and U.S. patent application Ser. No. 10/436,876, filed May 12, 2003, now issued as U.S. Pat. No. 7,069,070, the disclosures of which are incorporated by reference in their entirety.

FIELD OF THE INVENTION

This invention pertains to cardiac rhythm management devices such as pacemakers and implantable monitoring devices.

BACKGROUND

Heart rate variability (HRV) refers to the changes in the length of time between consecutive heart beats during sinus rhythm and is primarily due to the interaction between the sympathetic and parasympathetic arms of the autonomic nervous system. Measurement and analysis of heart rate variability is thus a useful and non-invasive tool for assessing the status of the autonomic nervous system.

The interval between successive heart beats, referred to herein as a BB interval, may be measured from a surface ECG or intracardiac electrogram as the time from the peak of one R wave representing ventricular depolarization to the peak of the next, referred to as an RR interval, or as the time from the peak of one P wave representing atrial depolarization to the peak of the next, referred to as an PP interval. Other measures of BB interval are possible and the present subject matter is not limited to the measures of BB interval based on morphological peaks described above. The variability of normal BB intervals (i.e., during sinus rhythm) can be determined and analyzed in several different ways in either the time domain or the frequency domain. Time domain measurements involve the computation of statistics based upon the individual BB intervals making up a BB time series such as the standard deviation of the BB intervals in the series. Frequency domain analysis employs methods such as the Fast Fourier Transform (FFT) or autoregressive analysis to analyze the frequency spectrum of the variability in the BB intervals. Analysis of the frequency spectrum of heart rate variability has proven to be particularly valuable in assessing the relative activities of the sympathetic and parasympathetic nervous systems in a subject. Such assessment of the state of autonomic balance is a useful function for implantable cardiac rhythm management devices such as pacemakers and implantable cardioverter/defibrillators to perform as it can be used to modify the manner in which therapy is delivered by the device or to predict the occurrence of arrhythmias.

Heart rate variability is a useful indicator of a subject's physiological state because it reflects the influence of internal feedback mechanisms within the body on the intrinsic heart rate produced at the sino-atrial node of the heart. Such feedback mechanisms are based on the interplay of the sympathetic and parasympathetic branches of the autonomic nervous system as well as various hormonal responses. Ectopic cardiac activity, such as premature atrial contractions (PAC's) and premature ventricular contractions (PVC's), are believed to be independent of the aforementioned internal feedback mechanisms. A heart rate variability metric calculated from a BB time series in which ectopic beats are present will be corrupted and may not accurately reflect the subject's true physiological state. For purposes of heart rate variability analysis, it is therefore desirable to exclude those BB intervals from a BB time series which are due to ectopic cardiac activity and are not the result of a normally conducted heart beat. It is with this problem that the present invention is primarily concerned.

SUMMARY

The present invention relates to an interval-based technique for removing ectopic or non-sinus events from a BB interval signal which may be implemented in an appropriately programmed implantable medical device. The technique involves filtering the BB intervals to exclude those BB intervals which are greater or less than a function of preceding BB intervals by a specified threshold value, the excluded BB intervals being deemed to be due to ectopic cardiac activity. Such a function of preceding BB intervals may be a statistic (e.g., a median or an average) computed from a plurality of preceding BB intervals. A heart rate variability metric may then be calculated from the filtered BB intervals. In one embodiment, the filtering is performed by comparing the present BB interval to a statistic computed from the plurality of previous BB intervals stored in a first-in-first-out buffer, where the buffer contains a maximum number N of preceding BB intervals. The buffer is then updated by removing the oldest interval and storing the present BB interval therein if the present BB interval was not excluded as ectopic.

DETAILED DESCRIPTION

Figure 1:
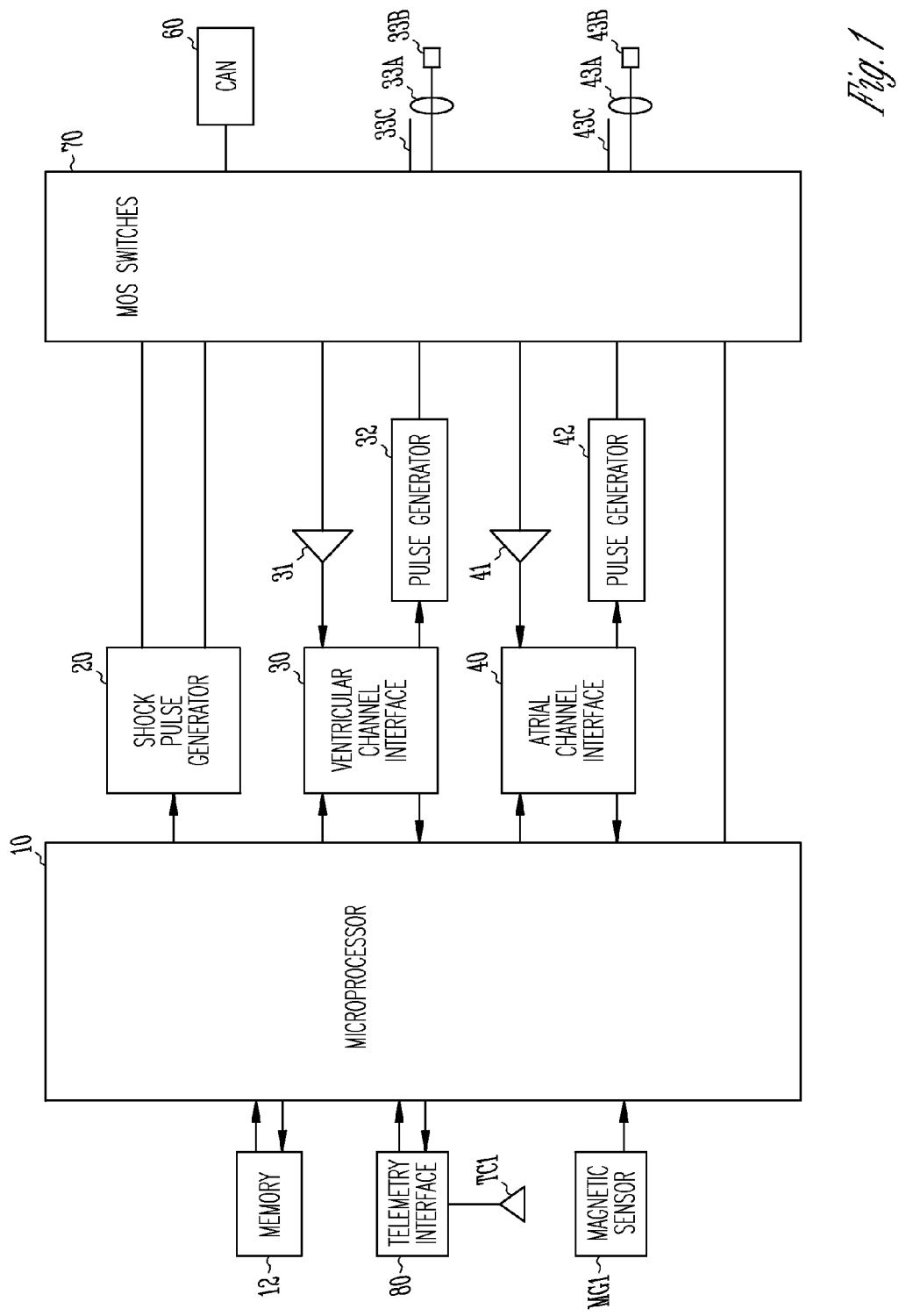
FIG. 1 is a block diagram of an exemplary cardiac rhythm management device for practicing the present invention.

As noted above, heart rate variability refers to the variability of the time intervals between successive heart beats during a sinus rhythm. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. If an implantable medical device is programmed to monitor the LF/HF ratio, the device can log a clinically significant event when the ratio exceeds a specified threshold value, as well as possibly automatically altering its mode of operation (e.g., initiating different therapies or performing more computationally intensive data analysis for arrhythmia prediction).

A series of BB interval values can be regarded as a discrete signal indexed by heartbeat such that each value of the signal represents a BB interval for a particular heartbeat. In order to properly analyze the frequency content of heart rate variability, however, the BB time series can be re-sampled at a specified sampling frequency so as to equalize the time intervals between interval values and thus convert the time series into a discrete time signal, where the sampling frequency is selected to meet the Nyquist criterion with respect to the frequencies of interest. Spectral analysis of such a BB interval signal can then be performed directly in the frequency domain using discrete Fourier transform or autoregression techniques in order to compute the LF/HF ratio. A time-domain technique for determining the high and low frequency components of the signal could also be used in which the BB interval signal is input to low band and high band digital filters and signals proportional to the power of the BB interval signal in each of the low frequency and high frequency bands are derived so that the LF/HF ratio may be computed.

Both frequency domain and time domain analysis performed as described above are computationally intensive, however, and require the storage of large amounts of BB interval data. Such methods may therefore not be practical in a typical implantable medical device which is a small battery-powered device with limited processing power. Statistical techniques for heart rate variability analysis that do not involve such processing overhead are described in above-cited U.S. patent application Ser. No. 10/436,876, where it should be appreciated that the term RR interval in that application can be taken to mean any measure of the interval between heart beats, referred to herein as a BB interval. Such techniques are used to generate surrogate parameters which represent different frequency components of a BB time series and from which the LF/HF ratio or other quantity may be calculated. The rMSSD statistic, for example, is defined as the square root of the mean of the squared successive differences of a BB time series:

$$rMSSD = E\{(BB_i - BB_{i-1})^2\}^{0.5}$$

where E is the expectation or mean value operator, and BB refers to the $i^{th}$ BB interval in the series. The square root step in the calculation can be omitted to give the $[rMSSD]^2$ parameter. By averaging the square of the successive interval-to-interval difference values in the BB time series, the rMSSD or $[rMSSD]^2$ statistic maximally reflects variations in the BB intervals that occur with each successive interval and progressively attenuates variations in the BB intervals that occur at lower frequencies. The frequency response represented by the rMSSD statistic is therefore greatest at the maximum frequency that can be represented in the time series (i.e., approximately one-half of the average heart rate, similar to the Nyquist frequency in a time series with regular intervals) and then decreases linearly with decreasing frequency so that lower frequency variability in the BB time series is not represented. Computation of the rMSSD or $[rMSSD]^2$ statistic thus captures a frequency range of heart rate variability which is similar to the HF band. The $SD_7$ statistic is defined as the standard deviation of the mean values of all successive 7-second segments in the BB time series, and $[SD_7]^2$ is the square of that standard deviation or variance. By computing mean values of the BB intervals over 7-second segments, the $[SD_7]^2$ statistic averages out the variations in the BB intervals that occur over time intervals equal to or smaller than 7 seconds (i.e., variations at frequencies higher than approximately 0.15 Hz), with the variations in the BB intervals occurring over longer intervals then being reflected by computation of the variance of those mean values. The $[SD_7]^2$ statistic thus captures those frequency components of the BB interval signal from some frequency above DC (since a variance calculation eliminates the DC component of a signal) to approximately $\frac{1}{7}$ or 0.15 Hz (i.e., a frequency with a period equal to the length of the 7-second segment). The $SD_{25}$ statistic is similarly defined as the standard deviation of the mean values of all successive 25-second segments in the BB time series, where $[SD_{25}]^2$ is the square of that standard deviation or variance. The $[SD_{25}]^2$ statistic thus captures those frequency components of the BB interval signal from some frequency above DC to approximately $\frac{1}{25}$ or 0.04 Hz (i.e., a frequency with a period equal to the length of the 25-second segment). If the $[SD_{25}]^2$ statistic is subtracted from the $[SD_7]^2$ statistic, the resulting parameter captures a frequency range of heart rate variability which is similar to the LF band.

The rMSSD, $[SD_{25}]^2$, and $[SD_7]^2$ statistics may thus serve as surrogates for the frequency components of a BB time series. An estimate of the LF/HF ratio may then be computed as:

$$\text{Estimated LF/HF} = K\{[SD_7]^2 - [SD_{25}]^2\}/[rMSSD]^2$$

where K is a constant. A linear regression analysis may be performed in which the estimated values are correlated with the actual spectrum of a BB time series to derive the value of K. Alternatively, the estimated LF/HF ratio may be compared with appropriately scaled threshold values in order to assess the autonomic balance of a subject, which eliminates the need for K in the calculation.

Heart rate variability metrics thus include parameters computed by time-domain filtering of a BB interval signal, parameters computed by frequency-domain analysis of an BB interval signal, and statistical parameters which serve as surrogates for different frequency components of the BB interval signal. Regardless of the particular heart rate variability metric, however, it is desirable to exclude from the BB interval signal those BB intervals which are due to ectopic cardiac activity such as PVC's. The present invention relates to a BB interval filtering technique for removing non-sinus rhythm events from a BB interval series used for heart rate variability analysis. A description of the technique is set forth below following a description of an exemplary hardware platform.

1. Exemplary Implantable Device Description

The present invention may be incorporated into any cardiac device with the capability of sensing cardiac electrical activity, including devices for monitoring only and those for delivering therapy in the form of electrical stimulation to the heart. For illustrative purposes, however, the invention will be described with reference to a dual-chamber pacemaker (i.e., one that senses and paces both the atria and ventricles).

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Cardiac rhythm management devices may also treat tachyarrhythmias, where the heart rate is too fast, by anti-tachycardia pacing and/or delivery of defibrillation shocks. Such devices are usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) and a RAM (random-access memory). The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer.

The embodiment shown in FIG. 1 has two sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. The channels may be configured as either atrial or ventricular channels. In an example configuration, an atrial sensing/pacing channel includes ring electrode 43a and tip electrode 43b of bipolar lead 43c, sense amplifier 41, pulse generator 42, and a channel interface 40. A ventricular sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator 20 is also interfaced to the controller for delivering defibrillation shocks through electrodes selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing. The switch matrix 70 may configure a channel for unipolar sensing or pacing by referencing an electrode of a unipolar or bipolar lead with the device housing or can 60.

The controller 10 controls the overall operation of the device in accordance with programmed instructions stored in memory. The controller 10 interprets electrogram signals from the sensing channels in order to control the delivery of paces in accordance with a pacing mode and/or deliver shock therapy in response to detection of a tachyarrhythmia such as ventricular fibrillation. The sensing circuitry of the device generates atrial and ventricular electrogram signals from the voltages sensed by the electrodes of a particular channel. An electrogram is analogous to a surface ECG and indicates the time course and amplitude of cardiac depolarization that occurs during either an intrinsic or paced beat. When an electrogram signal in an atrial or sensing channel exceeds a specified threshold, the controller detects a chamber sense (i.e., an atrial or ventricular sense, respectively), which pacing algorithms may employ to trigger or inhibit pacing and from which heart rates may be derived by measuring the intervals between senses. The measured intervals between successive ventricular senses or between successive atrial senses make up a BB time series. As described below, the controller may also be programmed to eliminate ectopic beats from the BB time series used to calculate heart rate variability metrics.

2. Interval-Based Filtering of Ectopic Events

A cardiac rhythm management device such as illustrated in FIG. 1 can be programmed to determine heart rate variability by analyzing data received from its sensing channels. The intervals between successive cardiac chamber senses, referred to as BB intervals, can be measured for a specified period of time or a specified number of beats and their variability analyzed. A typical BB time series, for example, would be made up of BB intervals over 24 hours or other period. As described above, a BB interval signal collected in this manner can be spectrally analyzed by the device in order to determine the frequency content in the LF and HF bands by either transforming the signal into the frequency domain, decomposing the signal with bandpass filters, or by calculating statistical parameters which serve as surrogates for the actual specific frequency components.

One way to derive a BB interval signal representing heart rate variability during a sinus rhythm is to remove ectopic beats with an event-based technique. For example, ectopic ventricular beats (i.e., premature ventricular contractions or PVCs) or ectopic atrial beats (i.e., premature atrial contractions or PACs) can be detected by monitoring whether an atrial sense (or P wave) precedes each ventricular sense (R wave). If two ventricular sense events occur with no atrial sense event between, the second ventricular sense is designated as a PVC. BB intervals adjacent to the PVC can then be removed from the BB interval series used for heart rate variability calculations (or changed to interpolated values). A similar approach can be applied when consecutive atrial senses are detected with no ventricular sense between. There are limitations with event-based ectopic beat removal, however. For example, ectopic events may be missed when a PVC following an atrial sense is deemed a sinus rhythm beat or when a PAC that is conducted through to the ventricle is classified as a sinus rhythm beat. Also, it is difficult to evaluate the performance of the implantable device based upon surface ECG Holter data because of the limited visibility of atrial events. In accordance with the present invention, a BB interval-based ectopic removal algorithm is used either instead of or in addition to the event-based technique described above. With this technique, BB intervals are classified as ectopic or not based on a history of previous BB intervals. An implantable medical device may thus be programmed to perform heart rate variability analysis by: 1) sensing electrical activity in a cardiac chamber and generating a chamber sense signal when the sensed electrical activity exceeds a predetermined threshold; 2) measuring time intervals between each pair of successive chamber senses, referred to as BB intervals, the measured BB intervals constituting an BB time series; 3) filtering the BB intervals to exclude those BB intervals which are greater or less than a statistic computed from a plurality of preceding BB intervals by a specified threshold value, the excluded BB intervals being deemed to be ectopic BB intervals which are due to ectopic cardiac activity; and, 4) computing a heart rate variability metric from the filtered BB intervals. The statistic computed from the plurality of BB intervals may be, for example, a median or a weighted average, and the threshold value may be a specified percentage of the calculated statistic. The device may also be programmed to maintain a count of ectopic events detected by the interval-based filtering or in conjunction with an event-based technique for diagnostic purposes.

Figure 2:
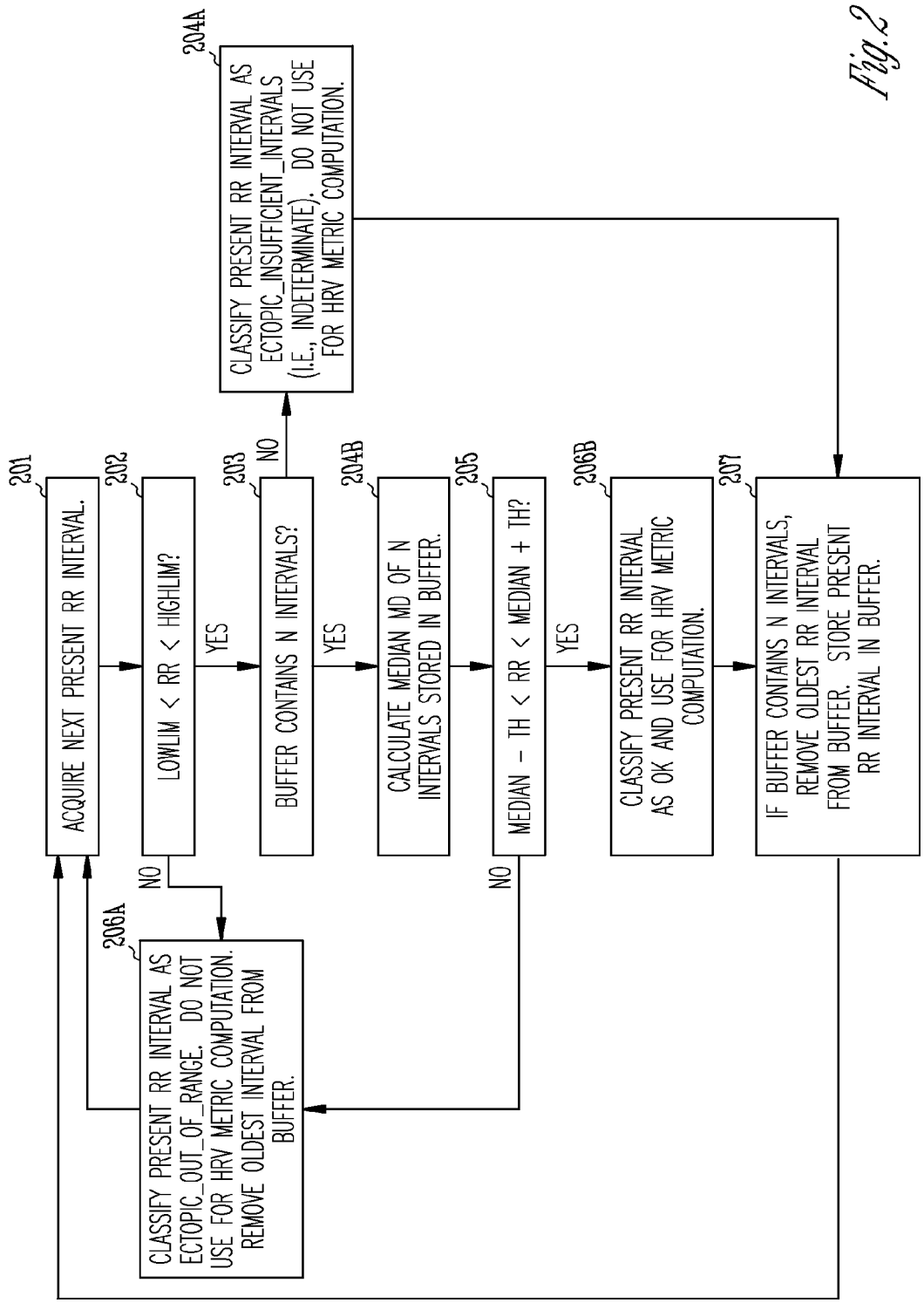
FIG. 2 illustrates an exemplary algorithm for filtering BB intervals to remove ectopic beats.

FIG. 2 illustrates an exemplary algorithm for removing ectopic events in accordance with the invention. Successive non-ectopic BB intervals are stored in a first-in-first-out (FIFO) buffer, and a median value of the stored intervals is computed for evaluating present BB intervals as they are collected. The buffer has a maximum capacity of N intervals where N is a specified integer. In a presently preferred embodiment, for reasons of both performance and computational efficiency, the number N is specified as three. Starting at step 201, the device acquires the next present BB interval. At step 202, the present BB interval is compared with a limit value HighLim and a low limit value LowLim. If the BB interval is above the high limit value or below the low limit value, the interval is classified as ectopic. Exemplary values for the high and low limit values are 2000 ms and 300 ms, respectively. Thus, if the present BB interval is not within the allowed range, step 206a classifies present BB interval as ECTOPIC_OUT_OF_RANGE, and the interval is not used for HRV metric computation. The oldest BB interval in the buffer is also removed, and the device returns to step 201 to collect the next BB interval. If the present BB interval is within the specified higher and lower limit values, the buffer is checked at step 203 to see if it contains N intervals. If so, the median MD of the N intervals in the buffer is computed at step 204b, and the present BB interval is compared with the computed median at step 205. If the present BB interval differs from the median MD by more than a specified threshold value Th (which may be a percentage of the computed median), the algorithm proceeds to step 206a so that the interval is classified as ECTOPIC_OUT_OF_RANGE. If not, the interval is classified as OK at step 206b so that it can be used in the calculation of a heart rate variability metric. Next, the buffer is updated at step 207 by: 1) if the buffer contains N intervals, removing the oldest BB interval from buffer, and 2) storing the present BB interval in the buffer. The algorithm then returns to step 201. Referring back to step 203, if the buffer does not contain N intervals, the present BB interval is not compared with a median computed from the intervals contained in the buffer. Instead, at step 204a, the present BB interval is classified ECTOPIC_INSUFFICIENT_INTERVALS (i.e., indeterminate) and not used for HRV metric computation. The algorithm then updates the buffer at step 207.

Figure 3:
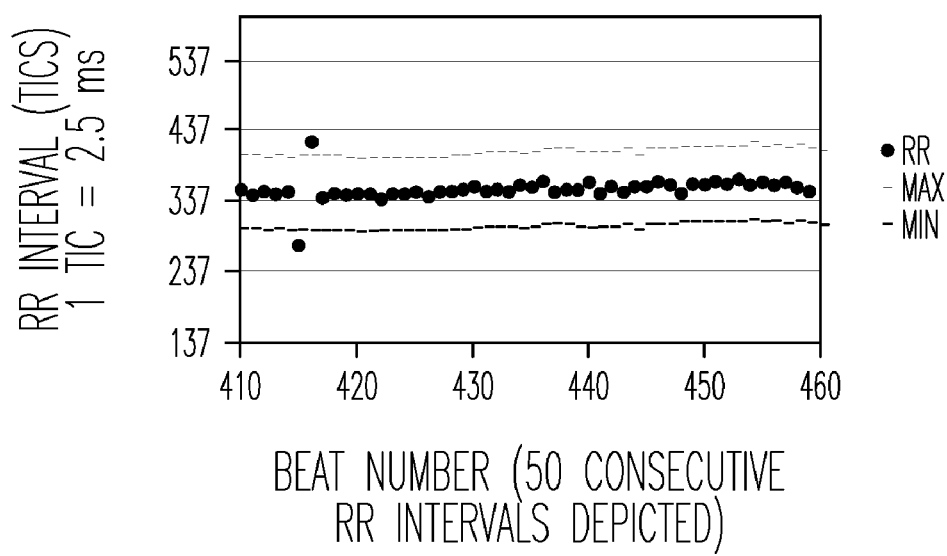
FIG. 3 is a graph showing the results of interval-based ectopic filtering of a representative RR interval series.

FIG. 3 is a graph showing the results of performing interval-based ectopic filtering of ectopic events as described above on a representative RR interval series. In this example, the statistic computed from preceding RR intervals is the median of the previous three non-ectopic RR intervals. An RR interval is classified as ectopic if it is greater or less than the median by a specified percentage of the computed median, shown graphically as those RR intervals which are above a maximum value Max or below a minimum value Min. Two such RR intervals are shown in the figure as being classified as ectopic.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method for operating a cardiac device, comprising:
    sensing electrical activity in a cardiac chamber and generating a chamber sense signal when the sensed electrical activity exceeds a predetermined threshold;
    measuring time intervals between each pair of successive chamber senses, referred to as BB intervals, the measured BB intervals constituting a BB time series;
    filtering the BB intervals to exclude particular BB intervals as ectopic using a buffer for storing a plurality of BB intervals by:
    1) acquiring a present BB interval,
    2) if the buffer contains less than N intervals, classifying the present BB interval as indeterminate, storing the indeterminately classified BB interval in the buffer, and returning to step 1,
    3) if the buffer contains N intervals, computing a statistic from the stored BB intervals and comparing the present BB interval to the computed statistic,
    4) excluding the present BB interval as an ectopic interval if the present BB interval is greater or less than the computed statistic by a specified threshold value, removing the oldest BB interval from the buffer, and returning to step 1,
    5) updating the buffer by removing the oldest BB interval and storing the present BB interval therein if the present BB interval is not excluded as ectopic and then returning to step 1; and
    computing a heart rate variability metric from the filtered BB intervals.

2. The method of claim 1 wherein the computed statistic is a median value of the plurality of preceding BB intervals.

3. The method of claim 1 wherein the computed statistic is a weighted average of the plurality of preceding BB intervals.

4. The method of claim 1 wherein the chamber senses are ventricular senses and the BB intervals are RR intervals.

5. The method of claim 1 wherein the specified threshold value is a specified percentage of the computed statistic.

6. The method of claim 1 further comprising filtering the BB intervals by:
    if the present BB interval is above or below specified upper and lower limit values, excluding the present BB interval as ectopic and removing the oldest BB interval from the buffer.

7. The method of claim 1 wherein the heart rate variability metric is a parameter computed by time-domain filtering of the filtered BB intervals.

8. The method of claim 1 wherein the heart rate variability metric is a parameter computed by frequency domain analysis of the filtered BB intervals.

9. The method of claim 1 wherein the heart rate variability metric is a statistical surrogate of a frequency component of the filtered BB intervals.

10. The method of claim 1 wherein the heart rate variability metric is a ratio of high-frequency and low-frequency components of the filtered BB intervals.

11. A cardiac rhythm management device, comprising:
    a sensing amplifier for sensing electrical activity in a cardiac chamber;
    a controller interfaced to the sensing amplifier which detects a chamber sense when the sensed electrical activity exceeds a predetermined threshold;
    wherein the controller is programmed with executable instructions for:

measuring time intervals between each pair of successive chamber senses, referred to as BB intervals, the measured BB intervals constituting a BB time series;

filtering the BB intervals to exclude particular BB intervals as ectopic using a buffer for storing a plurality of previous BB intervals and from which a statistic is computed, where the buffer can contain a maximum number N of such preceding BB intervals, by:

1) acquiring a present BB interval,
2) if the buffer contains less than N intervals, classifying the present BB interval as indeterminate, storing the indeterminately classified BB interval in the buffer, and returning to step 1,
3) if the buffer contains N intervals, computing a statistic from the stored BB intervals and comparing the present BB interval to the computed statistic,
4) excluding the present BB interval as an ectopic interval if the present BB interval is greater or less than the computed statistic by a specified threshold value, removing the oldest BB interval from the buffer, and returning to step 1,
5) updating the buffer by removing the oldest BB interval and storing the present BB interval therein if the present BB interval is not excluded as ectopic and then returning to step 1; and, computing a heart rate variability metric from the filtered BB intervals.

12. The device of claim 11 wherein the computed statistic is a median value of the plurality of preceding BB intervals.

13. The device of claim 11 wherein the computed statistic is a weighted average of the plurality of preceding BB intervals.

14. The device of claim 11 wherein the chamber senses are ventricular senses and the BB intervals are RR intervals.

15. The device of claim 11 wherein the specified threshold value is a specified percentage of the computed statistic.

16. The device of claim 11 wherein the controller is further programmed to filter the BB intervals by:
    if the present BB interval is above or below specified upper and lower limit values, excluding the present BB interval as ectopic and removing the oldest BB interval from the buffer.

17. The device of claim 11 wherein the heart rate variability metric is a parameter computed by time-domain filtering of the filtered BB intervals.

18. The device of claim 11 wherein the heart rate variability metric is a parameter computed by frequency domain analysis of the filtered BB intervals.

19. The device of claim 11 wherein the heart rate variability metric is a statistical surrogate of a frequency component of the filtered BB intervals.

20. The device of claim 11 wherein the heart rate variability metric is a ratio of high-frequency and low-frequency components of the filtered BB intervals.

* * * * *